(12) United States Patent
Wang et al.

(10) Patent No.: US 10,743,938 B2
(45) Date of Patent: Aug. 18, 2020

(54) IMAGE REGISTRATION AND AUGMENTED REALITY SYSTEM AND METHOD AUGMENTED REALITY THEREOF

(71) Applicant: MedicalTek Co. Ltd., Taichung (TW)

(72) Inventors: Yen-Yu Wang, Changhua County (TW); Kai-Che Liu, Changhua County (TW); Kumar Atul, Changhua County (TW); Li-Hsun Chen, Changhua County (TW)

(73) Assignee: Medicaltek Co., Ltd., Taichung (TW)

( * ) Notice: Subject to any disclaimer, the term of this patent is extended or adjusted under 35 U.S.C. 154(b) by 73 days.

(21) Appl. No.: 15/896,023

(22) Filed: Feb. 13, 2018

(65) Prior Publication Data

US 2018/0263698 A1  Sep. 20, 2018

(30) Foreign Application Priority Data

Mar. 20, 2017 (TW) .............................. 106109154 A

(51) Int. Cl.
*A61B 34/10* (2016.01)
*G06T 7/00* (2017.01)
(Continued)

(52) U.S. Cl.
CPC .............. *A61B 34/10* (2016.02); *A61B 90/36* (2016.02); *A61B 90/37* (2016.02); *G01B 11/2545* (2013.01); *G06T 7/0016* (2013.01); *G06T 7/33* (2017.01); *G06T 7/344* (2017.01); *G06T 17/00* (2013.01); *G06T 19/006* (2013.01); *G06T 19/20* (2013.01); *A61B 2034/104* (2016.02); *A61B 2034/105* (2016.02); *A61B 2090/365* (2016.02); *A61B 2090/366* (2016.02); *A61B 2090/367* (2016.02); *A61B 2090/371* (2016.02);
(Continued)

(58) Field of Classification Search
None
See application file for complete search history.

(56) References Cited

U.S. PATENT DOCUMENTS

2005/0054910 A1* 3/2005 Tremblay ............... A61B 5/055
                                                                        600/411
2007/0188603 A1* 8/2007 Riederer ................ G02B 21/22
                                                                         348/54
(Continued)

*Primary Examiner* — Michelle Chin
(74) *Attorney, Agent, or Firm* — Wang Law Firm, Inc.

(57) ABSTRACT

Disclosed is an image registration and an augmented reality system and an augmented reality method thereof which is suitable for solving the problem of spatial localization of the temporomandibular joint (TMJ) in arthroscopic surgery. The system comprises a three-dimensional scanning model building device, a stereoscopic image photographing device, a projection device and an arithmetic unit. The three-dimensional scanning model was constructed by preoperative or intraoperative imaging of the patient, and the surface three-dimensional model constructed by the stereoscopic image photographing device was spatially aligned to remove the surface (skin layer) of the three-dimensional image to display the TMJ image. Through the calibration of the stereoscopic image photographing device and the projection device, accurate, three-dimensional TMJ image location information is projected onto the patient's body to achieve the purpose.

10 Claims, 3 Drawing Sheets

(51) Int. Cl.
*G06T 7/33* (2017.01)
*G06T 17/00* (2006.01)
*G06T 19/00* (2011.01)
*G06T 19/20* (2011.01)
*A61B 90/00* (2016.01)
*G01B 11/25* (2006.01)
*H04N 13/204* (2018.01)
*A61B 90/50* (2016.01)

(52) U.S. Cl.
CPC ... *A61B 2090/372* (2016.02); *A61B 2090/374* (2016.02); *A61B 2090/3762* (2016.02); *A61B 2090/502* (2016.02); *G06T 2200/04* (2013.01); *G06T 2200/08* (2013.01); *G06T 2207/10021* (2013.01); *G06T 2207/10028* (2013.01); *G06T 2207/10081* (2013.01); *G06T 2207/30008* (2013.01); *G06T 2207/30088* (2013.01); *G06T 2207/30196* (2013.01); *G06T 2219/2008* (2013.01); *H04N 13/204* (2018.05)

(56) References Cited

U.S. PATENT DOCUMENTS

| | | | | |
|---|---|---|---|---|
| 2007/0189564 | A1* | 8/2007 | McBagonluri | H04R 25/552 381/322 |
| 2010/0137880 | A1* | 6/2010 | Nahum | A61B 34/70 606/130 |
| 2012/0016239 | A1* | 1/2012 | Barthe | A61B 8/0858 600/439 |
| 2013/0172731 | A1* | 7/2013 | Gole | A61B 5/0035 600/424 |
| 2015/0223903 | A1* | 8/2015 | Bell | A61B 5/0095 600/424 |

* cited by examiner

IMAGE REGISTRATION AND AUGMENTED REALITY SYSTEM AND METHOD AUGMENTED REALITY THEREOF

CROSS-REFERENCE TO RELATED APPLICATION

This application claims priority from the Taiwan Patent Application No. 106109154 filed on Mar. 20, 2017 at the Taiwan Intellectual Property Office, the content of which is hereby incorporated by reference in its entirety for all purposes.

BACKGROUND OF THE INVENTION

1. Field of the Invention

The present invention is related to an application of an image registration and an augmented reality system, and more particularly to an image registration and an augmented reality system for an arthroscopic surgery in order to achieve accurate spatial localizations.

2. Description of the Related Art

Three types of commonly used medical techniques for oral surgery are temporomandibular joint lavage, temporomandibular joint lysis and temporomandibular joint arthroscopy. The current conventional method is comprised of connecting a tragus with a lateral canthus through an imaginary line, travelling from the tragus to the lateral canthus along the imaginary line by 1 cm, subsequently travelling downwards by 2 mm, and setting the final position as the entry point. With respect to the method, there are several adjustments required due to fundamental differences in head types of humans of various races or under real and diverse conditions. On the other hand, another method is performed through palpation, in which the front of the tragus is touched by the practitioner's hands, after which an upper join space between temporomandibular joints through mandibular movements may be defined. Regardless of either of the methods chosen, the entry point sometimes needs to be checked repeatedly by means of injecting saline or through other preliminary confirmation means. Consequently, in each surgery, surgical instruments may not precisely enter the temporomandibular joints, and thus medical staff may need to rely on experiences or go through multiple attempts to conduct the surgery. Hence, uncertainties of the surgery may occur.

As a result, in order to assist the medical staff in determining the correct positions of the temporomandibular joints, an image auxiliary localization technique is essential in reducing uncertainties due to human factors.

SUMMARY OF THE INVENTION

In accordance with the issues of known techniques above, the purpose of the present invention is to provide an image registration and augmented reality system, comprising a three-dimensional scanning model building device, a stereoscopic image photographing device, an arithmetic unit, a projection device and a control device. The three-dimensional scanning model building device scans the cranium of a body to generate a plurality of anatomic images, and builds a three-dimensional scanning model according to the plurality of anatomic images. The stereoscopic image photographing device captures a plurality of skin surface images of the cranium and ears of the body, and builds a surface three-dimensional model according to the plurality of skin surface images. The arithmetic unit corrects and aligns the three-dimensional scanning model and the surface three-dimensional model according to a plurality of structural reference points on surfaces of a temporal portion and the ears of the body, and combines the aligned three-dimensional scanning model with the aligned surface three-dimensional model to visualize a three-dimensional image. The projection device is corrected according to a location of the stereoscopic image photographing device so as to project the three-dimensional image onto a corresponding skin surface of the body. The control device is electrically connected with the arithmetic unit and the projection device. Furthermore, after the three-dimensional image is projected onto the skin surface of the body, the control device controls the arithmetic unit to remove the surface three-dimensional model of the three-dimensional image, and display at least an internal tissue image of the body of the three-dimensional image through the projection device.

Preferably, the projection device is spatially and geometrically calibrated, so as to be calibrated to the same coordinate system as that of the stereoscopic image photographing device.

Preferably, the internal tissue image of the body includes a cranium image and a mandibular image, such that medical staff are able to locate an entry point for surgical instruments according to the internal tissue image of the body.

Preferably, the three-dimensional scanning model building device includes anatomic image scanning devices for computerized tomography or nuclear magnetic resonance imaging.

In accordance with the purpose described above, the present invention provides another image registration and augmented reality system, comprising a three-dimensional scanning model building device, a stereoscopic image photographing device, an arithmetic unit, a projection device and a control device. The three-dimensional scanning model building device scans a part of a body to generate a plurality of anatomic images, and builds a three-dimensional scanning model according to the plurality of anatomic images. The stereoscopic image photographing device captures a plurality of skin surface images of the part of the body, and builds a surface three-dimensional model according to the plurality of skin surface images. The arithmetic unit corrects and aligns the three-dimensional scanning model and the surface three-dimensional model according to a plurality of structural reference points on surfaces and around an organ having a three-dimensional structure of the part of the body, and combines the aligned three-dimensional scanning model with the aligned surface three-dimensional model to visualize a three-dimensional image. The projection device is corrected according to a location of the stereoscopic image photographing device so as to project the three-dimensional image onto a corresponding skin surface of the body. The control device is electrically connected with the arithmetic unit and the projection device. Furthermore, after the three-dimensional image is projected onto the skin surface of the body, the control device controls the arithmetic unit to remove the surface three-dimensional model of the three-dimensional image, and display at least an internal tissue image of the body of the three-dimensional image through the projection device.

Preferably, the three-dimensional image includes images of each tissue layer of the body.

Preferably, the projection device includes a monitor, a projector, or a head mounted display for displaying the three-dimensional scanning model, the surface three-dimensional model, the three-dimensional image and the body.

Preferably, the surfaces of the part of the body include a temporal portion of the body.

Preferably, the organ having the three-dimensional structure of the part of the body includes ears of the body.

Moreover, in accordance with the purpose described above, the present invention further provides a method of image registration and augmented reality, comprising steps as follows:

A. Scanning a cranium of a body by utilizing a three-dimensional scanning model building device to generate a plurality of anatomic images, and then building a three-dimensional scanning model according to the plurality of anatomic images.

B. Capturing a plurality of skin surface images of the cranium and ears of the body by utilizing a stereoscopic image photographing device, and then building a surface three-dimensional model according to the plurality of skin surface images.

C. Correcting and aligning the three-dimensional scanning model and the surface three-dimensional model according to a plurality of structural reference points on surfaces of a temporal portion and the ears of the body through an arithmetic unit, and then combining the aligned three-dimensional scanning model with the aligned surface three-dimensional model to visualize a three-dimensional image.

D. Projecting the three-dimensional image onto a corresponding skin surface of the body.

E. Removing the surface three-dimensional model of the three-dimensional image, and then displaying at least an internal tissue image of the body of the three-dimensional image.

DESCRIPTION OF THE PREFERRED EMBODIMENTS

Figure 1:
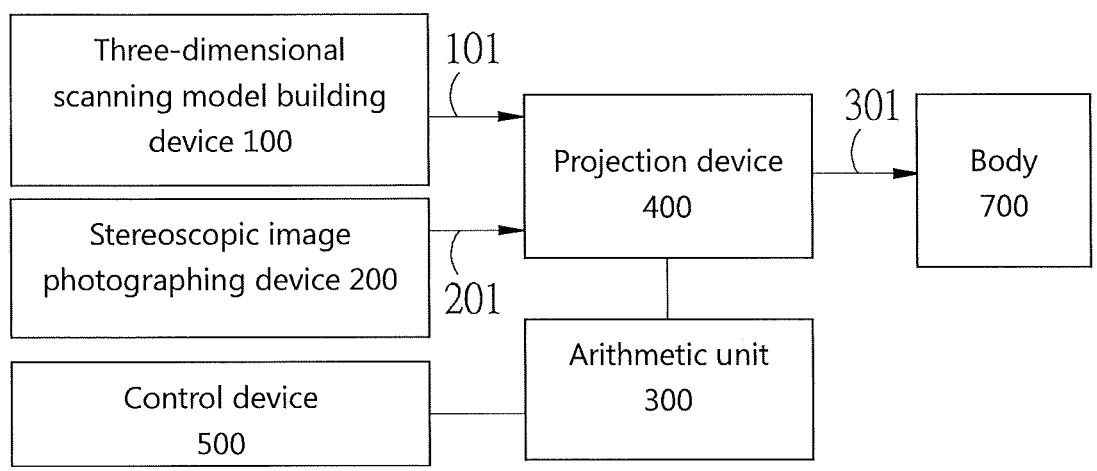
FIG. 1 is a schematic diagram of the system in accordance with one embodiment of the present invention.

For a better understanding of the technical features, details and advantages of the present invention as well as the achievable effects thereof, the present invention is explicitly described below in the form of embodiments with reference to the appended drawings. The drawings present schematics of the present invention and assist with the specification, whereby what is depicted in the drawings does not necessarily conform to the real dimensions and precise layout of the present invention. That is, the actual scope of practical implementation of the present invention is not confined by the dimensions and layout depicted in the appended drawings.

The embodiments of the image registration and augmented reality system and the augmented reality method thereof will be more explicitly described below via referring to the related drawings. In order to make the description below easier to understand, the same components will be marked by the same symbols in the following embodiments.

Figure 2:
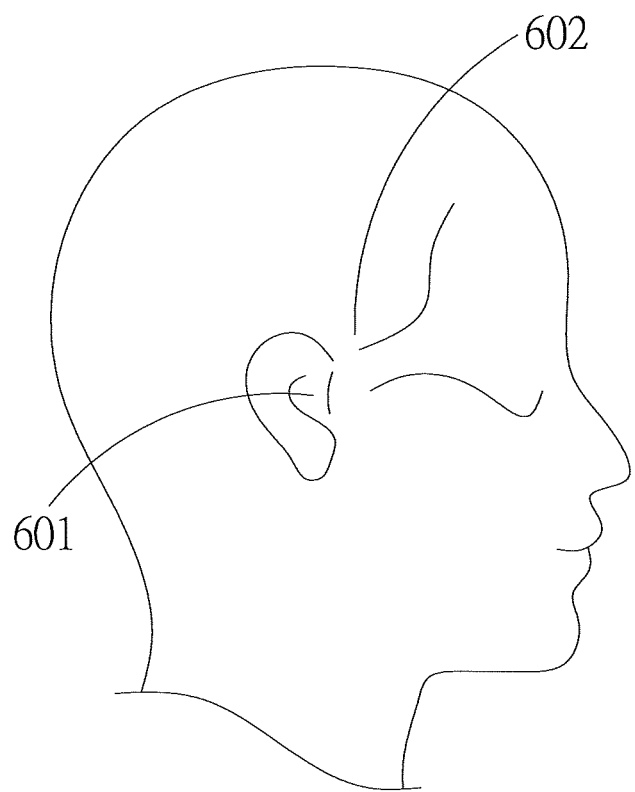
FIG. 2 is a schematic diagram of the reference point in accordance with one embodiment of the present invention.

Please refer to FIG. 1 and FIG. 2, which are the schematic diagram of the system in accordance with one embodiment of the present invention and the schematic diagram of the reference point in accordance with one embodiment of the present invention, respectively.

As illustrated in FIG. 1 and FIG. 2, the image registration and augmented reality system of the present invention comprises a three-dimensional scanning model building device 100, a stereoscopic image photographing device 200, an arithmetic unit 300, a projection device 400 and a control device 500.

The three-dimensional scanning model building device 100 of the present invention may scan a cranium of a body 700 to generate a plurality of anatomic images, and then build a three-dimensional scanning model 101 according to the plurality of anatomic images. Furthermore, the three-dimensional scanning model building device 100 includes anatomic image scanning devices for computerized tomography (CT) or nuclear magnetic resonance imaging (MRI). Hence, generally speaking, before a surgery is conducted, the anatomic image scanning devices for computerized tomography (CT) or nuclear magnetic resonance imaging (MRI) may scan a patient to generate a plurality of anatomic images thereof, and then a three-dimensional scanning model 101 may be built according to the plurality of anatomic images. On the other hand, the three-dimensional scanning model 101 may be built by means of volume rendering or other three-dimensional building manner.

The stereoscopic image photographing device 200 may capture a part of the body 700 through scanning to generate a plurality of anatomic images, and then build a surface three-dimensional model 201 according to a plurality of skin surface images.

The arithmetic unit 300 may correct and align the three-dimensional scanning model 101 and the surface three-dimensional model 201 according to a plurality of structural reference points on surfaces and around an organ having a three-dimensional structure of the part of the body 700, and combine the aligned three-dimensional scanning model 101 with the aligned surface three-dimensional model 201 to visualize a three-dimensional image 301.

More specifically, the surfaces of the part of the body 700 include a temporal portion 602 of the body 700, and the organ with a three-dimensional structure includes ears 601 of the body 700.

Consequently, as illustrated in FIG. 2, the stereoscopic image photographing device 200 may capture a plurality of skin surface images of the cranium and ears 601 of the body 700. Since the arithmetic unit 300 may correct and align the three-dimensional scanning model 101 and the surface three-dimensional model 201 according to a plurality of structural reference points on surfaces and around an organ having a three-dimensional structure of the part of the body 700, the arithmetic unit 300 may accordingly correct and align the three-dimensional scanning model 101 and the surface three-dimensional model 201 according to a plurality of structural reference points on surfaces of the temporal portion 602 and the ears 601 of the body 700.

Moreover, the stereoscopic image photographing device 200 may be a depth camera composed of a multi-camera system, cameras and infrared camera for three-dimensional reconstruction and projective reconstruction of surfaces thereof via the camera-projector system with structure light or other devices capable of reconstructing three-dimensional surface images, so as to perform reconstructions of the surface three-dimensional model 201.

The projection device 400 may be corrected according to the location of the stereoscopic image photographing device 200, so as to project the three-dimensional image 301 onto a corresponding skin surface of the body 700. The control device 500 may be electrically connected with the arithmetic unit 300 and the projection device 400, wherein the control device 500 may be a master control computer in charge of controlling the total system and managing the information transmission.

Hence, after the three-dimensional image 301 is projected onto the skin surface of the body 700, the arithmetic unit 300 may be controlled by the control device 500 to remove the surface three-dimensional model 201 of the three-dimensional image 301. Besides, the three-dimensional image 301 includes images of each tissue layer of the body 700. More specifically, the internal tissue image of the body 700 includes the cranium image, the mandibular image and images of other tissue layers, such that medical staff may accurately locate the entry point of surgical instruments according to the internal tissue image of the body 700.

Furthermore, in order to make the projection device 400 able to project the three-dimensional image 301 onto the correct position, the projection device 400 needs to be spatially and geometrically calibrated, so as to be located in the same coordinate system as the stereoscopic image photographing device 200. The spatial and geometric calibration is about conducting a conversion of the projected image in coordination with external matrix between a camera and a projector, so as to make sure the consistency between the projection location and the stereoscopic image photographing device 200. Consequently, the arithmetic unit 300 may conduct an external matrix transformation between the projection device 400 and the stereoscopic image photographing device 200, so as to ensure the three-dimensional image 301 is correctly projected. Since a person skilled in the art should be familiar with the known technique of the spatial and geometric calibration, detailed content thereof is not described herein.

Additionally, the image registration and augmented reality system of the present invention may further comprise a display device, which may display the images projected by the projection device 400 for viewing, so as to check whether each procedure and component meet the requirements.

In other embodiments of the present invention, the projection device 400 of the image registration and augmented reality system may not include the display device described above, and replace the display device with a head mounted display, which is capable of displaying the three-dimensional scanning model 101, the surface three-dimensional model 201, the three-dimensional image 301 and the body 700. Hence, medical staff, such as surgeons may observe the images directly through the head mounted display, so as to proceed with the surgeries successfully.

Figure 3:
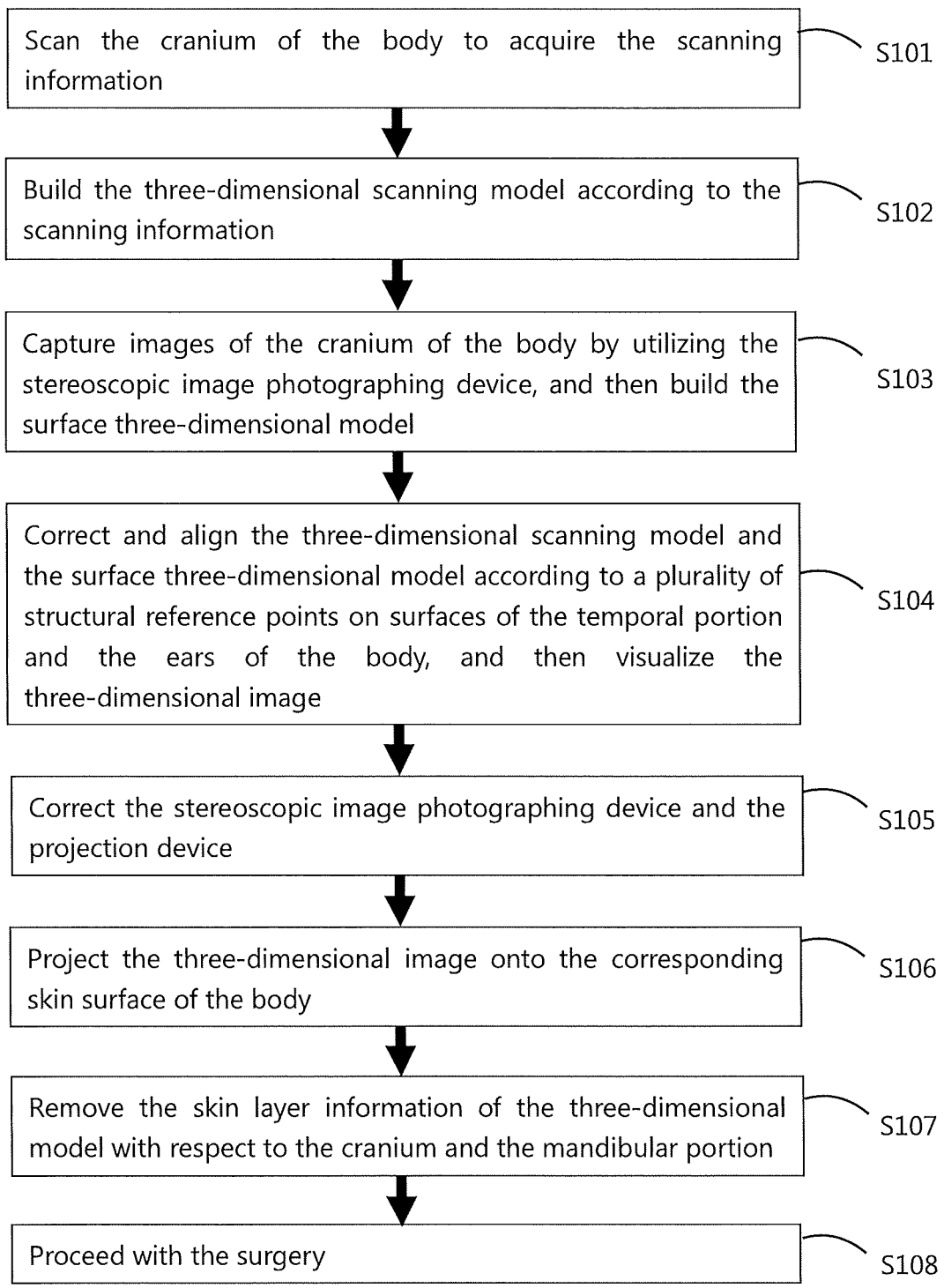
FIG. 3 is a flow chart of the method of image registration and augmented reality in accordance with one embodiment of the present invention.

Please refer to FIG. 3, which is the flow chart of the method of image registration and augmented reality in accordance with one embodiment of the present invention. As illustrated in FIG. 3, the method of image registration and augmented reality comprises steps as follows:

Step S101: Scanning the cranium of the body 700 by utilizing the three-dimensional scanning model building device 100 to generate a plurality of anatomy images.

Step S102: Building the three-dimensional scanning model 101 according to the plurality of anatomy images.

Step S103: Capturing a plurality of skin surface images of the cranium and ears 601 of the body 700 by utilizing the stereoscopic image photographing device 200, and then building the surface three-dimensional model 201 according to the plurality of skin surface images.

Step S104: Correcting and aligning the three-dimensional scanning model 101 and the surface three-dimensional model 201 according to a plurality of structural reference points on surfaces of the temporal portion 602 and the ears 601 of the body 700 through the arithmetic unit 300, and then combining the aligned three-dimensional scanning model 101 with the aligned surface three-dimensional model 201 to visualize the three-dimensional image 301.

Step S105: Correcting the stereoscopic image photographing device 200 and the projection device 400.

Step S106: Projecting the three-dimensional image 301 onto the corresponding skin surface of the body 700.

Step S107: Removing the surface three-dimensional model 201 of the three-dimensional image 301, and then displaying at least the internal tissue image of the body 700 of the three-dimensional image 301.

Step S108: Medical staff may perform medical procedure according to the internal tissue image of the body 700.

To be especially noted is that, except for the steps with explanation of causal relationship, other steps may be performed through any permutation thereof. For example, the step 105 of correcting the stereoscopic image photographing device 200 and the projection device 400 need not to be performed after the step 104, but may also be finished before the step 104.

On the basis of descriptions above, the image registration and augmented reality system and the augmented reality method thereof of the present invention may allow users to utilize the image localization and augmented reality during the arthroscopic surgery or other cranium surgeries, saving time that was spent determining the entry point of endoscopes or surgical instruments, and simultaneously providing the users with explicit localization information and image information of related positions thereof, and thus achieving the purpose of accurate localization before each surgery.

The descriptions above are merely for the purpose of exemplifying rather than limiting the present invention. Therefore, numerous modifications, variations and enhancements can be made thereto by those skilled in the art without departing from the spirit and scope of the invention set forth in the claims.

What is claimed is:

1. An image registration and augmented reality system, comprising:
   a three-dimensional scanning model building device, scanning a cranium of a body to generate a plurality of anatomic images, and building a three-dimensional scanning model according to the plurality of anatomic images;
   a stereoscopic image photographing device, capturing a plurality of skin surface images of the cranium and ears of the body, and building a surface three-dimensional model according to the plurality of skin surface images;
   an arithmetic unit correcting and aligning the three-dimensional scanning model and the surface three-dimensional model according to a plurality of structural reference points on surfaces of a temporal portion and the ears of the body, and combining the aligned three-dimensional scanning model with the aligned surface three-dimensional model to visualize a three-dimensional image;
   a projection device, calibrated and aligned according to a location of the stereoscopic image photographing device so as to project the three-dimensional image onto a corresponding skin surface of the body; and a control device, electrically connected with the arithmetic unit and the projection device;

wherein after the three-dimensional image is projected onto the skin surface of the body, the control device controls the arithmetic unit to remove the surface three-dimensional model of the three-dimensional image, and display at least an internal tissue image of the body of the three-dimensional image through the projection device.

2. The image registration and augmented reality system of claim 1, wherein the projection device is spatially and geometrically calibrated, so as to be located in a same coordinate system as that of the stereoscopic image photographing device.

3. The image registration and augmented reality system of claim 1, wherein the internal tissue image of the body includes a cranium image and a mandibular image, such that medical staff is able to locate an entry point of surgical instruments according to the internal tissue image of the body.

4. The image registration and augmented reality system of claim 1, wherein the three-dimensional scanning model building device includes anatomic image scanning devices for computerized tomography or nuclear magnetic resonance imaging.

5. An image registration and augmented reality system, comprising:
- a three-dimensional scanning model building device, scanning a part of a body to generate a plurality of anatomic images, and building a three-dimensional scanning model according to the plurality of anatomic images;
- a stereoscopic image photographing device, capturing a plurality of skin surface images of the part of the body, and building a surface three-dimensional model according to the plurality of skin surface images;
- an arithmetic unit correcting and aligning the three-dimensional scanning model and the surface three-dimensional model according to a plurality of structural reference points on surfaces and around an organ having a three-dimensional structure of the part of the body, and combining the aligned three-dimensional scanning model with the aligned surface three-dimensional model to visualize a three-dimensional image;
- a projection device, corrected according to a location of the stereoscopic image photographing device so as to project the three-dimensional image onto a corresponding skin surface of the body; and
- a control device electrically connected with the arithmetic unit and the projection device;

wherein after the three-dimensional image is projected onto the skin surface of the body, the control device controls the arithmetic unit to remove the surface three-dimensional model of the three-dimensional image, and display at least an internal tissue image of the body of the three-dimensional image through the projection device.

6. The image registration and augmented reality system of claim 5, wherein the three-dimensional image includes images of each tissue layer of the body.

7. The image registration and augmented reality system of claim 5, wherein the projection device includes a monitor, a projector, or a head mounted display for displaying the three-dimensional scanning model, the surface three-dimensional model, the three-dimensional image and the body.

8. The image registration and augmented reality system of claim 5 wherein the surfaces of the part of the body include a temporal portion of the body.

9. The image registration and augmented reality system of claim 5, wherein the organ having the three-dimensional structure of the part of the body includes ears of the body.

10. A method of image registration and augmented reality, comprising:
- A. Scanning a cranium of a body by utilizing a three-dimensional scanning model building device to generate a plurality of anatomic images, and then building a three-dimensional scanning model according to the plurality of anatomic images;
- B. Capturing a plurality of skin surface images of the cranium and ears of the body by utilizing a stereoscopic image photographing device and then building a surface three-dimensional model according to the plurality of skin surface images;
- C. Correcting and aligning the three-dimensional scanning model and the surface three-dimensional model according to a plurality of structural reference points on surfaces of a temporal portion and the ears of the body through an arithmetic unit and then combining the aligned three-dimensional scanning model with the aligned surface three-dimensional model to visualize a three-dimensional image;
- D. Projecting the three-dimensional image onto a corresponding skin surface of the body; and
- E. Removing the surface three-dimensional model of the three-dimensional image, and displaying at least an internal tissue image of the body of the three-dimensional image.

* * * * *